United States Patent [19]

Zee

[11] Patent Number: Plant 5,629

[45] Date of Patent: Jan. 7, 1986

[54] APPLE TREE 'SUMMER GRANNY'

[75] Inventor: Theodore J. Zee, R.D. #1, Box 398, Glassboro-Richwood Rd., Glassboro, N.J. 08028, by Douglas S. Zee, legal representative

[73] Assignees: Douglas Zee, Jr.; Michael C. Zee, both of Glassboro, N.J. ; part interest to each

[21] Appl. No.: 460,573

[22] Filed: Jan. 24, 1983

[51] Int. Cl.[4] ..... A01H 5/00

[52] U.S. Cl. ..... Plt./34

[58] Field of Search ..... Plt./34

*Primary Examiner*—James R. Feyrer

*Attorney, Agent, or Firm*—Frank B. Robb

[57] ABSTRACT

A summer apple tree variety producing fruit having hard flesh, greenish-yellow general color effect, juicy, bruise-resistant, long-keeping, mostly round shape, with good resistance to insects and no evidence of scab or russet.

4 Drawing Figures

BACKGROUND AND DESCRIPTION OF THE INVENTION

The present invention relates to a new and distinct variety of apple tree, discovered by me in the cultivated orchard of Douglas S. Zee, Sr. in the vicinity of Glassboro, N.J. as a seedling which had developed into a full tree, and which is designated as "Summer Granny".

The tree was growing in a block of Idared apple trees and was particularly distinctive because of its greenish-yellow fruit, which upon first discovery was noted to be particularly hard and because the tree had bloomed somewhat later than the Idared variety, in fact some five days later.

The fruit was found to be particularly hard and when handled it was noted that it did not bruise easily in contrast to the usual summer apples which bruise very easily. It was subsequently determined that the fruit had very good keeping qualities as would be expected in a hard apple but in this instance particularly true since apples have been kept for as long as 180 days under normal storage conditions.

I have caused the tree to be asexually reproduced by budding, and found that in successive propagations the characteristics previously noted have been maintained and have come true in such reproduction. In addition to the improvement in keeping qualities there are certain other aspects which make the apple a good commercial variety for local market use and, particularly useful in the culinary arts.

The apples have been found to be free from russet and are not bothered by insects.

The fruit produced may be particularly compared with the varieties "Lodi" and "Star", both unpatented which are known varieties of summer apples and are subject to bruising and have short keeping characteristics.

In the asexual reproduction effected, as stated the characteristics are maintained in the new and distinct variety, and they may be summarized by stating that they are improvements over previously known varieties in the following aspects:

1. The fruit is hard and juicy.
2. The fruit is exceptionally resistant to bruising.
3. The long-keeping quality of the fruit is particularly valuable having been kept 180 days under ordinary storage conditions.

4. The fruit is of mostly round shape, greenish-yellow in general over-all appearance.
5. The fruit is characterized by good resistance to insects and freedom from scab and russet.
6. The trees bloom later than the Idared (unpatented) variety by approximately five days and earlier than the Golden Delicious.

The accompanying drawing shows a group of fruit, wherein.

Figures 1, 2, 3, 4:
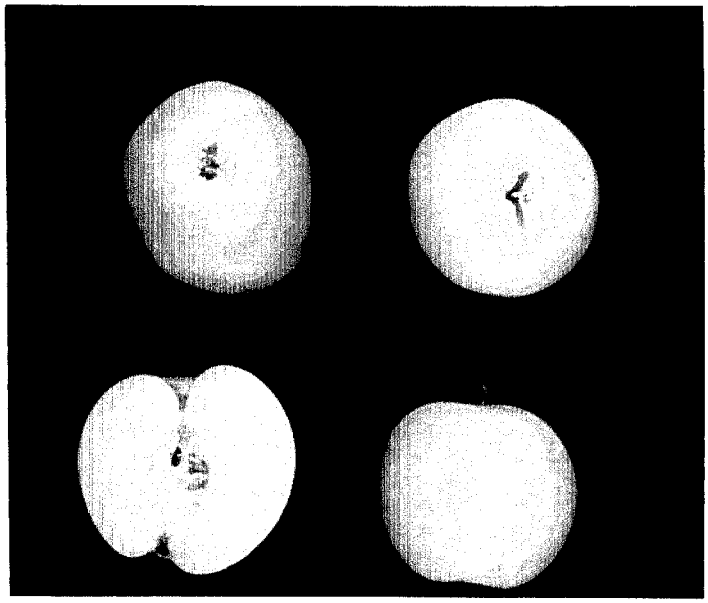
FIG. 1 is a bottom view of an apple of the variety herein.
FIG. 2 is a top view of my new variety.
FIG. 3 is a vertical sectional view showing the apple flesh, and seed arrangement.
FIG. 4 is a side view of the apple.

The apples are depicted in color as nearly true as is reasonably possible to disclose the same in a color illustration of this character.

There follows a detailed description of my new variety with color terminology in accordance with the Munsel Color Cascade published by MacBeth Kolmorgen Corp., the color terminology where used, being that of general color terms having ordinary dictionary significance if and when appropriate.

It may be noted that inasmuch as color is not particularly significant although overall it is of value, such description is minimal herein as the other characteristics are the most important aspects hereof.

Locality where grown and observed: Glassboro, N.J. and in the orchard of Douglas S. Zee, Sr.

Date of first picking: July 25.

Date of last picking: Aug. 1.

Tree: Medium size; vigorous; spreading; rapid growing; hardy; very productive; regular bearer.

*Trunk.*—Medium and smooth.

*Branches.*—Medium; smooth; medium branching.

*Color.*—Reddish brown.

*Lenticels.*—Medium quantity and size.

Foliage:

*Leaves.*—Length (about) 4 inches–$2\frac{1}{4}$ inches wide. Large: wide, long; oval; thick.

*Color.*—Upper side — 20-15. Lower side — 23-12.

*Margin.*—Crenate.

*Petiole.*—Penate and coarsely serrate.

*Petiole.*—Length — $\frac{7}{8}$ inches; medium thickness.

Flowers:

*Dates of first and full bloom.*—Apr. 15 and Apr. 18.
*Size.*—Large.
*Color.*—White.

Fruit:

*Maturity when described.*—Eating — Hard; over-ripe, about Sept. 1.
*Size.*—Axial diameter $2\frac{7}{8}$ inches. Transverse— $2\frac{3}{4}$ inches.
*Form.*—Uniform; symmetrical.
*Cavity.*—Symmetrical — Not pubescent.
*Markings.*—None of significance.
*Basin.*—Symmetrical and rounded.
*Stem.*—Clubbed — Medium length about $\frac{3}{4}$ inches.
*Brachts.*—Recurved; Small, open and mostly wanting.
*Calyx.*—Some pubescence.
*Eye.*—Small; partially closed.
*Skin.*—Thick; tough; smooth; glossy.
*Dots.*—Small and obscure. Circular, if any.
*Color of dots where present.*—Greenish-white.
*Bloom.*—Wanting.
*General color effect.*—Greenish-yellow 23-7 ground and over-all 24-4.

Flesh: Juicy.

*Color.*—Greenish tint.
*Texture.*—Firm, fine.
*Flavor.*—Acid; mild.

*Aroma.*—Distant.
*Quality.*—Good.

Core:

*Sessile.*—Median.
*Bundle area.*—Medium.
*Bundles.*—Color — Greenish.
*Calyx.*—Narrow. Stamens — Obscure. Auxiliary cavity — Wanting. Number of perfect — 2. Number in one cell 13 2. Color — Dark brown.

Use: Market; local; and culinary.

Keeping quality: Superior and can be classed as very exceptional. Number of days in ordinary storage 180 days or more. The fruit being hard and resisting bruising as it does may be contrasted with "Lodi" and "Star", both unpatented varieties.

Resistance to insects — Good; diseases — no scab observed.

I claim:

1. A new and distinct variety of Summer Apple Tree substantially as herein shown and described, characterized particularly as to novelty by the unique combination in the fruit produced thereby, of hard, juicy flesh, exceptional bruise resistance, and long-keeping quality, mostly round shape, greenish-yellow general over-all appearance, good resistance to insects and freedom from scab and russet.

* * * * *